United States Patent [19]
Hutchison et al.

[11] Patent Number: 6,156,751
[45] Date of Patent: Dec. 5, 2000

[54] CERTAIN TRICYCLIC SUBSTITUTED DIAZABICYCLO (3.2.1) OCTANE DERIVATIVES

[75] Inventors: Alan Hutchison, Madison; Jun Yuan, Clinton; Raymond F. Horvath, North Branford, all of Conn.

[73] Assignee: Neurogen Corporation, Brandford, Conn.

[21] Appl. No.: 09/393,789

[22] Filed: Sep. 10, 1999

Related U.S. Application Data

[63] Continuation of application No. 08/429,060, Apr. 26, 1995, Pat. No. 5,952,501, which is a continuation of application No. 08/001,259, Jan. 6, 1993, abandoned.

[51] Int. Cl.[7] .................... A61K 31/495; C07D 247/00
[52] U.S. Cl. ................. 514/250; 514/249; 514/450
[58] Field of Search .................... 514/249, 250, 514/450

[56] References Cited

U.S. PATENT DOCUMENTS

| | | | |
|---|---|---|---|
| 5,344,831 | 9/1994 | Satoh et al. | 514/249 |
| 5,952,501 | 9/1999 | Hutchison et al. | 544/349 |

FOREIGN PATENT DOCUMENTS

| | | |
|---|---|---|
| 2 099 683 | 3/1972 | France . |
| 06306070 | 11/1994 | Japan . |
| 7100196 | 7/1972 | Netherlands . |

*Primary Examiner*—Mukund J. Shah
*Assistant Examiner*—Pavanaram K Sripada
*Attorney, Agent, or Firm*—McDonnell Boehnen Hulbert & Berghoff; Steven J. Sarussi

[57] ABSTRACT

This invention encompasses compounds of the formula:

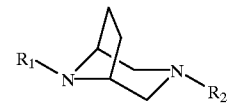

where either $R_1$ or $R_2$ represents

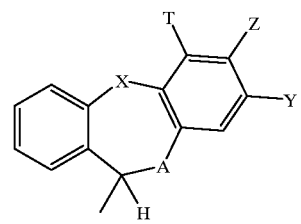

and the other represents hydrogen or straight or branched chain lower alkyl having 1–6 carbon atoms; and X is oxygen, methylene, or NH;

Y is represents various inorganic and organic substituents;

Z is hydrogen, amino or $NHR_6$ where $R_6$ is lowere alkyl having 1–6 carbon atoms;

T is hydrogen, halogen, hydroxy, or lower alkoxy having 1–6 carbon atoms; and

A is methylene, carbonyl or CHOH.

These compounds are selective partial agonists or antagonists at brain monoamine receptor subtypes or prodrugs thereof and are useful in the diagnosis and treatment of affective disorders such as schizophrenia and depression as well as certain movement disorders such as Parkinsonism. Furthermore compounds of this invention may be useful in treating the extrapyramidal side effects associated with the use of conventional neurolepticagents. These compounds show unexpectedly atypical antipsychotic profiles (clozapine-like) in the animal models described in this patent.

5 Claims, 1 Drawing Sheet

Compound 1

Compound 2

Compound 3

CERTAIN TRICYCLIC SUBSTITUTED DIAZABICYCLO (3.2.1) OCTANE DERIVATIVES

This is a continuation of application Ser. No. 08/429,060, filed Apr. 26, 1995 now U.S. Pat. No. 5,952,501; which is a continuation of U.S. Ser. No. 08/001,259, filed Jan. 6, 1993 abandoned.

BACKGROUND OF THE INVENTION

1. Field of the Invention

This invention relates to certain tricyclic substituted diazabicyclo[3.2.1] octane derivatives which selectively bind to certain monoamine receptor subtypes. This invention also relates to pharmaceutical compositions comprising such compounds. It further relates to the use of such compounds in treating affective disorders such as schizophrenia and depression as well as certain movement disorders such as Parkinsonism. Furthermore compounds of this invention may be useful in treating the extrapyramidal side effects associated with the use of conventional neuroleptic agents. These tricyclic substituted diazabicyclo[3.2.1] octane derivatives of the invention interact with certain noradrenalin, dopamine and serotonin receptor subtypes. The demonstration of atypical antipsychotic profiles (clozapine-like) in key animal behavioral models is also described for certain compounds of this invention.

2. Description of the Related Art

Schizophrenia and psychosis are terms used to describe a group of illnesses of unknown origin which affect approximately 2.5 million people in the United States. These disorders of the brain are characterised by a variety of symptoms which are classified as positive symptoms (disordered thought, hallucinations and delusions) and negative symptoms (social withdrawal and unresponsiveness). These disorders have an age of onset in adolescence or early adulthood and persist for many years. The disorders tend to become more severe during the patients lifetime and can result in prolonged institutionalization. In the US today, approximately 40% of all hospitalized psychiatric patients suffer from schizophrenia.

During the 1950's physicians demonstrated that they could successfully treat psychotic patients with medications called neuroleptics; this classification of antipsychotic medication was based largely on the activating (neuroleptic) properties of the nervous system by these drugs. Subsequently, neuroleptic agents were shown to increase the concentrations of dopamine metabolites in the brain suggesting altered neuronal firing of the dopamine system. Additional evidence indicated that dopamine could increase the activity of adenylate cyclase in the corpus striatum, an effect reversed by neuroleplic agents. Thus, cummulative evidence from these and later experiments strongly suggested that the neurotransmitter dopamine was involved in schizophrenia.

One of the major actions of antipsychotic medication is the blockade of dopamine receptors in brain. Several dopamine systems appear to exist in the brain and at least three classes of dopamine receptors appear to mediate the actions of this transmitter. These dopamine receptors differ in their pharmacological specificity. They were originally classified based upon the known pharmacology of different chemical series. The class of compounds known as butyrophenones, which includes many potent antipsychotic drugs, are weakly active at the adenylate cyclase-activating dopamine receptor, now known as a D1 dopamine receptor. In contrast, they labelled other dopamine receptors (called D2 receptors) in the subnanomolar range and a third type D3 in the nanomolar range. Phenothiazines possess nanomolar affinity for all three types of dopamine receptors. Other drugs have been developed with great specificity for the D1 subtype receptor.

Recently, a new group of drugs (such as sulpiride and clozapine) have been developed with a lesser incidence of extrapyramidal side effects than classical neuroleptics. In addition, there is some indication that they may be more beneficial in treating negative symptoms in some patients. Since all D2 blockers do not possess a similar profile, hypotheses underlying the differences have been investigated. The major differences have been in the anticholinergic actions of the neuroleptics as well as the possililiity that the dopamirie receptors may differ in motor areas from those in the limbic areas thought to mediate the antipsychotic responses. The existence of the D3 and other as yet undiscovered dopamine receptors may contribute to this profile. Some of the atypical compounds possess similar activity at both D2 and D3 receptors. The compounds of the present invention fall into this general class of molecules.

Using molecular biological techniques it has been possible to clone cDNAs coding for each of the pharmacologically defined receptors. There are at least two forms of D1, and two forms of D2 dopamine receptors. In addition. there is .it least one form of D3 dopamine receptor.

The tricyclic substituted diazabicyclo[3.2.1] octane derivatives of the invention possess differential affinities for each receptor subtype as well as for certain other noradrenergic and seretonergic receptor subtypes.

French patent application 71.27825 discloses compounds of the general formula:

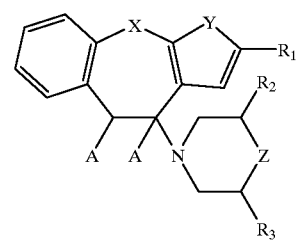

and their salts, in which:

X signifies either an atom of sulfur, or an atom of oxygen, or an atom of selenium;

Y signifies either a —CH=CH— group, or an atom of sulfur

Z signifies either a single bond, or a group —CH$_2$—, or an atom of oxygen, or NR4;

A signifies either hydrogen or, while being bonded together, yet another bond;

R$_1$ signifies either hydrogen, or an atom of halogen, or trifluoromethyl, or an amino group, or an alkyl group, or an alkoxy group;

R$_2$ and R$_3$ signify either an atom of hydrogen or, while being bonded together, a bivalent part —CH2CH2—;

R$_4$ signifies either an alkyl group, a hydroxyalkyl having from 1–4 carbon atoms, cycloalkyl, cycloalkylalkyl having 3–6 carbon atoms, phenyl or benzyl.

SUMMARY OF THE INVENTION

This invention provides novel compounds of Formula I which interact with dopamine receptor subtypes.

The invention provides pharmaceutical compositions comprising compounds of Formula I. The invention also provides compounds useful in treating affective disorders such as schizophrenia and depression as well as certain movement disorders such as Parkinsonism. Furthermore compounds of this invention may be useful in treating the extrapyramidal side effects associated with the use of conventional neuroleptic agents. Accordingly, a broad embodiment of the invention is directed to a compound of Formula I:

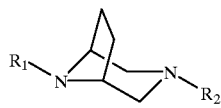

wherein:
$R_1$ represents hydrogen or straight or branched chain lower alkyl having 1–6 carbon atoms and $R_2$ represents a group of the formula:

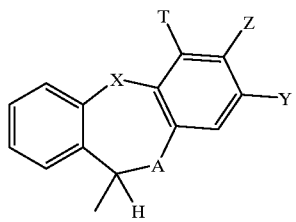

or
$R_2$ represents hydrogen or straight or branched chain lower alkyl having 1–6 carbon atoms and $R_1$ represents a group of the formula:

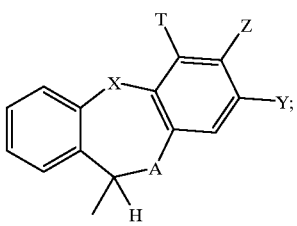

X is oxygen, methylene, or NH;
Y is halogen, straight or branched chain lower alkyl having 1–6 carbon atoms, lower alkoxy having 1–6 carbon atoms, hydroxy. amino, aminoalkyl where the alkyl is straight or branched chain lower alkyl having 1–6 carbon atoms, $SR_3$, $SOR_3$, or $SO_2R_3$ where $R_3$ is straight or branched chain lower alkyl having 1–6 carbon atoms, or $SO_2NR_4R_5$ where $R_4$ and $R_5$ are the same or different and represent hydrogen or straight or branched chain lower alkyl having 1–6 carbon atoms;
Z is hydrogen, amino or $NHR_6$ where $R_6$ is straight or branched chain lower alkyl having 1–6 carbon atoms;
T is hydrogen, halogen, hydroxy, or lower alkoxy having 1–6 carbon atoms; and
A is methylene, carbonyl or CHOH.

These compounds are selective partial agonists or antagonists at brain monoamine receptor subtypes, or prodrugs thereof, and are useful in the diagnosis and treatment of affective disorders such as schizophrenia and depression as well as certain movement disorders such as Parkinsonism. Furthermore compounds of this invention can be useful in treating the extrapyramidal side effects associated with the use of conventional neuroleptic agents. Unexpectedly, these compounds show atypical antipsychotic profiles (clozapine-like) in the animal models described herein.

DETAILED DESCRIPTION OF THE INVENTION

The novel compounds encompassed by the instant invention can be described by general formula I:

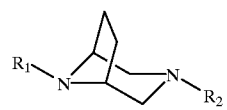

wherein:
$R_1$ represents hydrogen or straight or branched chain lower alkyl having 1–6 carbon atoms and $R_2$ represents a group of the formula:

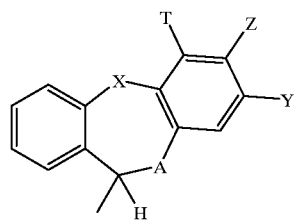

or
$R_2$ represents hydrogen or straight or branched chain lower alkyl having 1–6 carbon atoms and $R_1$ represents a group of the formula:

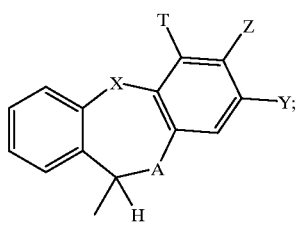

X is oxygen, methylene, or NH;
Y is halogen, straight or branched chain lower alkyl having 1–6 carbon atoms, lower alkoxy having 1–6 carbon atoms, hydroxy. amino, aminoalkyl where the alkyl is straight or branched chain lower alkyl having 1–6 carbon atoms, $SR_3$, $SOR_3$, or $SO_2R_3$ where $R_3$ is straight or branched chain lower alkyl having 1–6 carbon atoms, or $SO_2NR_4R_5$ where $R_4$ and $R_5$ are the same or different and represent hydrogen or straight or branched chain lower alkyl having 1–6 carbon atoms;
Z is hydrogen, amino or $NHR_6$ where $R_6$ is straight or branched chain lower alkyl having 1–6 carbon atoms;

T is hydrogen, halogen, hydroxy, or lower alkoxy having 1–6 carbon atoms; and

A is methylene, carbonyl or CHOH.

The present invention also encompasses compounds of general formula

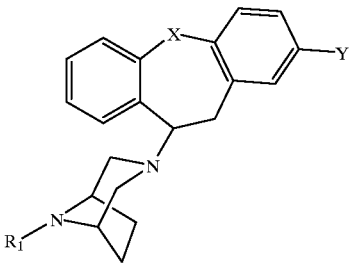

wherein

X is oxygen, methylene, or NH;

Y is halogen or straight or branched chain lower alkyl having 1–6 carbon atoms; and $R_1$ represents hydrogen or straight or branched chain lower alkyl having 1–6 carbon atoms.

The present invention also encompasses compounds of general formula

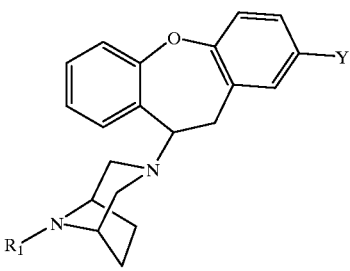

wherein

Y is halogen or straight or branched chain lower alkyl having 1–6 carbon atoms; and $R_1$ represents hydrogen or straight or branched chain lower alkyl having 1–6 carbon atoms.

The present invention also encompasses compounds of general formula

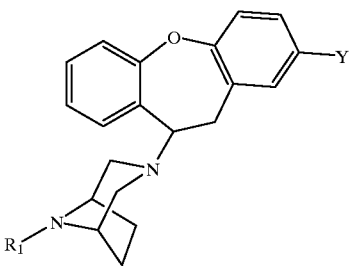

wherein

Y is halogen or straight or branched chain lower alkyl having 1–6 carbon atoms; and $R_1$ represents methyl.

Non-toxic pharmaceutical salts include salts of acids such as hydrochloric, phosphoric, hydrobromic, sulfuric, sulfinic, formic, toluene sulfonic, hydroiodic, acetic and the like.

Those skilled in the art will recognize a wide variety of non-toxic pharmaceutically acceptable addition salts.

By lower alkyl in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By halogen in the present invention is meant fluorine, bromine, chlorine, and iodine.

Figure 1:
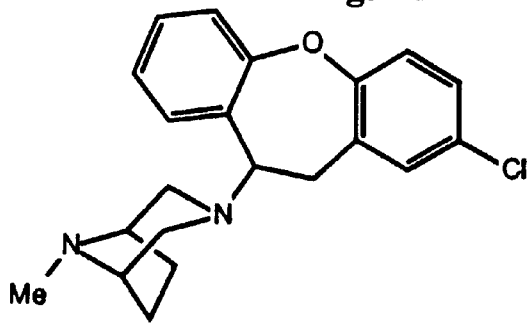
FIGS. 1–3 show representative tricyclic substituted diazabicyclo-[3.2.1] octane derivatives of the present invention.
Figure 2:
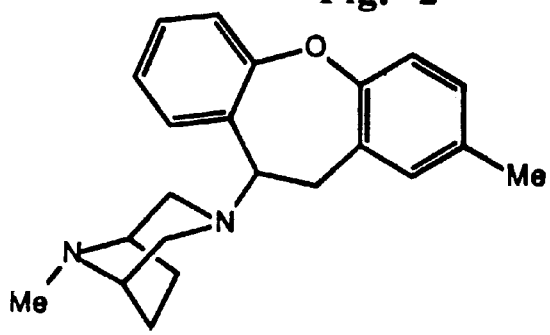
Figure 3:
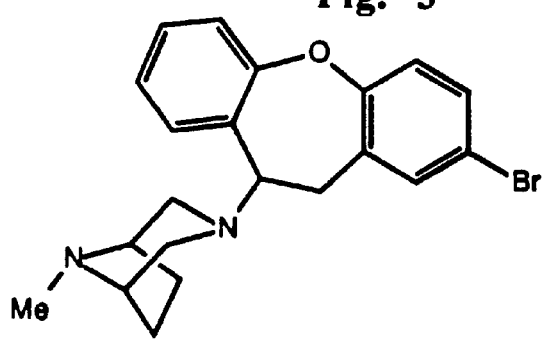

Representative compounds of the present invention, which are encompassed by Formula I, include, but are not limited to the compounds in FIG. 1 and their pharmaceutically acceptable salts. The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

The pharmaceutical utility of compounds of this invention are indicated by the following models which are predictive of compounds with a clozapine like atypical neuroleptic profile.

1. Antagonism of Amphetamine-Induced Rearing and Locomotor Activity

Rats injected with moderate doses of the dopamine (DA) receptor agonist amphetamine show an increase in locomotor activity and rearing. Most drugs that are effective in alleviating schizophrenic symptoms are DA receptor blockers that reverse the hyperactivity associated with amphetamine. Greenshaw et al., Animal Models For Assessing Anxiolytic, Neuroleptic, and Antidepressant Drug Action, in Neuromethods: Analysis of Psychiatric Drugs, edited by Boulton et al., vol. 10, pp. 379–427, Humana Press, New Jersey, 1988. It is believed that the ability of antipsychotic drugs to reduce this hyperactivity in rodents is related to the drug's clinical efficacy in humans. Because of this potential relationship, the following animal model is included in the battery of tests utilized to detect and evaluate compounds that may possess antipsychotic properties.

For each compound, it is necessary to test 4 to 5 doser to ensure that the behaviorally effective dose range that inhibits amphetamine-induced activity is reliably determined. Furthermore, to ensure the reliability of the effect, approximately five to eight rats are tested at each dose. Each rat is tested only once to avoid the effects of tolerance and sensitization, phenomena that are commonly observed with dopaminergic compounds.

The compound to be analyzed is administered either orally or subcutaneously (SC) to male Sprague-Dawley rats (250–325 g). Following a predetermined time interval (15 to 60 minutes, depending on the drug and the route of administration), the rat is then given an intraperitoneal injection of 2.0 mg/kg amphetamine. Rats given oral injections are food-deprived for 24 hours prior to the oral administration to enhance drug absorption. Immediately after the amphetamine injection, each rat is placed into the center of a transparent Plexiglass activity monitor, (40×40×40 cm) available from Oninitech Electronics, Columbus, Ohio. Horizontal activity is measured by two sets of 16 infrared photocell emitters and detectors (2.5 cm apart) located 5 cm above the floor. Vertical activity (e.g., rearing) is measured by a another set of 16 photocells (2.5 cm apart) located 15 cm above the floor. Photocell beam interruptions are automatically recorded and analyzed by a Digiscan Analyser. Each rat is monitored for 60 min.

The results produced by the compounds of the invention are shown below in Table I and are compared to the effects obtained from known DA receptor blockers (clozapine, haloperidol and eticlopride) that have various efficacies in treating schizophrenia.

2. Antagonism of Apomorphine-Induced Stereotype ($ED_{50}$ AAIS)

Rats injected with the dopamine (DA) receptor agonist apomorphine develop stereotypical patterns of behavior. The patterns involve a restriction of forward locomotion and prolonged bouts of continuous sniffing, licking or gnawing of surfaces and objects in the rat's environment. Szechtman et al., Psychobiology, 16: 164–173 (1988). Most drugs that are effective in alleviating schizophrenic symptoms are DA receptor blockers that inhibit the development of apomorphine-induced stereotype in rodents. It is believed that the anti-stereotypical effects of these drugs in rodents is related to the extrapyramidal side effects associated with antipsychotic use in humans. Ljungberg et al., Psychopharmacology, 56: 239–247 (1978). Because of this relationship, the apomorphine-induced stereotype animal model is included in the battery of tests designed to detect and evaluate compounds that may produce extrapyramidal side effects in humans.

For each compound, it is necessary to test 4 to 5 doses to ensure that the behaviorally effective dose range that inhibits apomorphine-induced stereotype is determined reliably. Furthermore, to ensure the reliability of the effect, approximately five to eight rats are tested at each dose. Each rat is tested only once to avoid the distorting effects of tolerance and sensitization. phenomena that are commonly observed with dopaminergic compounds. The compound is administered either orally or subcutaneously (SC) to male Sprague-Dawley rats (250–325 g). Following a predetermined time interval (15 to 60 minutes depending on the drug and the route of administration), the rat is then given a SC injection of 1.0 mg/kg apomorphine. Rats given oral injections are food-deprived for 24 hours prior to the oral administration to enhance drug absorption. Immediately after the apomorphine injection, the rat is placed into the center of an open field and observed every 5 minutes for 1 hour.

Stereotypy is scored using a standardized rating scale similar to the one described by Costall and Naylor. Psychopharmacologia (Berl.) 43: 69–74 (1975). Stereotypy is measured using a 0–5 rating scale based on the presence or absence of sniffing, licking or gnawing in which snout contact is maintained with either the floor, wooden ledge or wall. Scores are determined as follows: 0=no stereotypy; 1=discontinuous sniffing (sniffing is interrupted for an interval greater than 5 sec), 2=discontinuous licking or gnawing (sniffing interrupted for an interval greater than 5 sec), 3=continuous sniffing, 4=continuous sniffing with discontinuous licking or gnawing, 5=continuous gnawing. Total scores for activity and stereotypy are obtained by summing the number of crossovers and ratings, respectively, over the thirteen 1-minute observation periods.

The stereotypy produced by the compounds of the invention is shown below in Table I. The results produced by the compounds of the invention are compared to the effects obtained from known antipsychotics (clozapine, haloperidol and eticlopride) that have various liabilities for producing extrapyramidal side effects.

The ratios of the $ED_{50}$'s determined in the assay systems described above are predictive of typical versus atypical profiles for potential neuroleptic candidates. In general, compounds which have stereotypy:hyperactivity $ED_{50}$ ratios greater than ten are considered to have a clozapine like atypical profile. Ratios determined for the compounds of the invention are shown below in Table I. Data for clozapine and several conventional neuroleptic compounds are shown for comparison.

A compound encompassed within the disclosure of French patent application No. 71.27825 was synthesized and evaluated using the assays described above. This prior art compound is designated Compound A for purposes of comparison and has the formula:

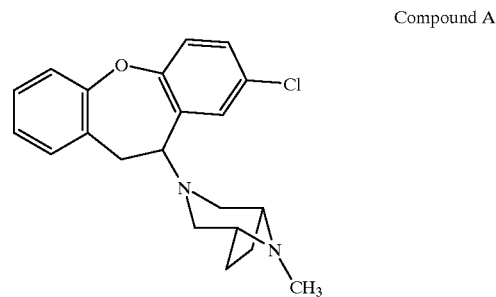

Compound A

This compound possesses a typical neuroleptic profile which is comparable to conventional neuroleptic agents. The profile shown by Compound A is different than the clozapine-like atypical antipsychotic profiles shown by clozapine and the compounds of this invention. This data is presented in Table I.

TABLE I

| Compound | $ED_{50}$ Hyperactivity (mg/kg sc) | $ED_{50}$ Stereotypy (mg/kg sc) | Ratio |
| --- | --- | --- | --- |
| Clozapine | 1.49 | 26.9 | 18 |
| Haloperidol | 0.038 | 0.036 | 0.94 |
| Raclopride | 0.048 | 0.044 | 0.92 |
| R-Octoclothepin | 0.80 | 0.18 | 4.4 |
| Prior Art Cpd A | 0.22 | 0.69 | 3.1 |
| Compound 1[1] | 0.84 | >40 | >48 |
| Compound 2[1] | 0.41 | 12.7 | 31 |
| Compound 3[1] | 2.15 | >22 | >10 |

[1]Compound numbers relate to compounds shown in FIGS. 1–4.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methyrlcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monolcate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water. Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

An illustration of the preparation of compounds of the present invention is given in Schemes I and II. Those having skill in the art will recognize that the starting materials may be varied and additional steps employed to produce compounds encompassed by the present invention.

Scheme I

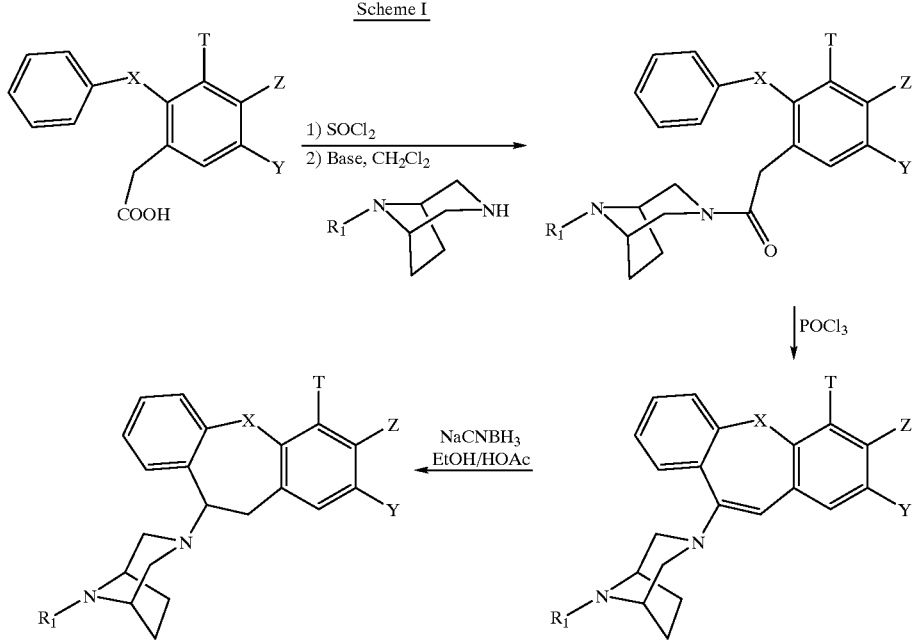

Scheme II

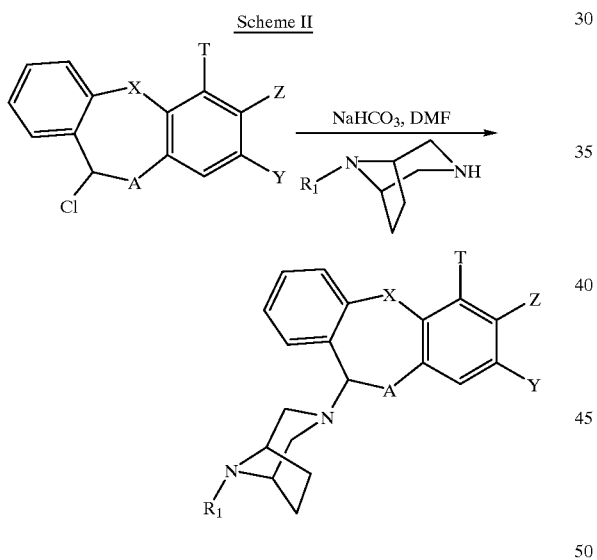

where:

R₁ represents hydrogen or straight or branched chain lower alkyl having 1–6 carbon atoms.

X is oxygen, methylene, or NH;

Y is halogen, straight or branched chain lower alkyl having 1–6 carbon atoms, lower alkoxy having 1–6 carbon atoms, hydroxy, amino, aminoalkyl where the alkyl is straight or branched chain lower alkyl having 1–6 carbon atoms, $SR_3$, $SOR_3$, or $SO_2R_3$ where $R_3$ is straight or branched chain lower alkyl having 1–6 carbon atoms, or $SO_2NR_4R_5$ where $R_4$ and $R_5$ are the same or different and represent hydrogen or straight or branched chain lower alkyl having 1–6 carbon atoms;

Z is hydrogen, amino or $NHR_6$ where $R_6$ is straight or branched chain lower alkyl having 1–6 carbon atoms;

T is hydrogen, halogen, hydroxy, or lower alkoxy having 1–6 carbon atoms; and

A is methylene, carbonyl or CHOH.

The invention is illustrated further by the following examples which are not to be construed as limiting the invention in scope or spirit to the specific procedures and compounds described in them.

Example I

Amide A1

A mixture of 5-Chloro-2-Phenoxyphenylacetic acid (1.5 g) and thionyl chloride (15 mL) was stirred at room temperature for 16 h. The excess thionyl chloride was removed in vacuo, toluene was added and the solvent was removed in vacuo again. The crude acid chloride was dissloved in 10 mL of methylene chloride and added dropwise to a mixture of 8-Methyl-3,8-diazabicyclo(3.2.1)octane dibydrochloride (1.2 g) and diisopropylethylamine (5 mL) in methylene chloride (15 mL) at 0° C. After 1 h at room temperature the reaction was washed with NaHCO3 solution, dried over magnesium sulfate and the solvent was removed in vacuo to afford the amide A1 as a glassy solid. The corresponding hydrochloride salt was prepared from HCl in ethyl acetate.

Example II

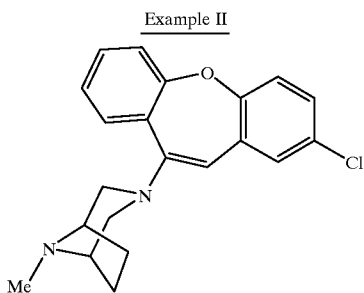

A mixture of the Amide A1 hydrochloride (from Example 1) and phosphorous oxychloride (25 mL) was refluxed with stirring for 30 h. The excess reagent was removed in vacuo and the residue was treated with ice cold ammonium hydroxide and ether. The ether layer was dried over magnesium sulfate and the solvent was removed in vacuo to afford 3-(2-Chloro-10,11-dibenzo[b,f]oxepin-10-yl)-8-methyl-3,8-diazabicyclo(3.2.1)octane as a glassy solid.

Example III

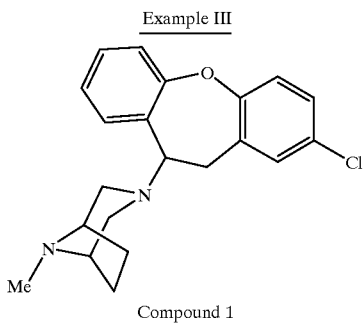

Compound 1

A mixture of 3-(2-Chloro-10,11-dibenzo[b,f]oxepin-10-yl)-8-methyl-3,8-diazabicyclo(3.2.1)oclane (1.5 g), sodium cyanoborohydride (1.1 g), ethanol (45 mL) and acetic acid (1.7 mL) was heated at 80° C. for 1 h. The reaction mixture was concentrated in vacuo, and 3N HCl and ether was added. The aqueous layer was basified and the product was extracted with ether. After drying over magnesium sulfate the solvent was removed in vacuo. The residue is dissolved in ethanol and 500 mg of maleic acid was added and the mixture was warmed until a clear solution is obtained. After dilution of this mixture with ether and cooling at −20° C. overnight, 3-(2-Chloro-10,11-dihydro-dibenzo[b,f]oxepin-10-yl)-8-methyl-3,8-diazabicyclo(3.2.1)octane monomaleate (Compound 1) melting at 161–170° C. was obtained as white crystals.

Example IV

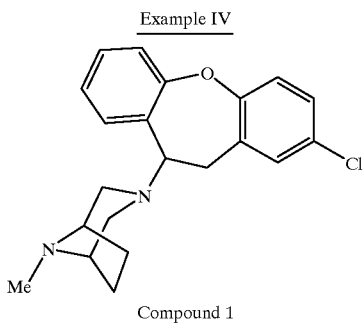

Compound 1

A mixture of 2,10-Dichloro-10,11-dihydro-dibenz[b,f]oxepin (3.2 g), 8-Methyl-3,8-diazabicyclo(3.2.1)octane dihydrochloride (1.6 g), sodium bicarbonate (10 g), and dimethylformamide (40 mL) was stirred at 100° C. for 1 h. After cooling, the reaction mixture was poured onto water, made basic with NaOH and the products are extracted with ether. The ether layer was extracted with 3N HCl, the aqueous layer is basified and the basic product was reextracted with ether. After drying over magnesium sulfate the solvent was removed in vacua. The residue is dissolved in ethanol and 500 mg of maleic acid was added and the mixture was warmed until a clear solution is obtained. After dilution of this mixture with ether and cooling at −20° C. overnight, 3-(2-Chloro-10,11-dihydro-dibenzo[b,f]oxepin-10-yl)-8-methyl-3,8-diazabicyclo(3.2.1)octane monomaleate (Compound 1) melting at 169–170° C. was obtained as white crystals.

Example V

The following compounds are prepared essentially as set forth above in Examples I–IV:

a) 3-(2-Methyl-10,11-dihydro-dibenzo[b,f]oxepin-10-yl)-8-methyl-3,8-diazabicyclo(3.2.1)octane monomaleate (Compound 2) melting at 179–184° C.
b) 3 (2-Bromo-10,11-dihydro-dibenzo[b,f]oxepin-10-yl)-8-methyl-3,8-diazabicyclo(3.2.1)octane monomaleate (Compound 3).
c) 3-(2-Fluoro-10,11-dihydro-dibenzo[b.f]oxepin-10-yl)-8-methyl-3,8-diazabicyclo(3.2.1)octane (Compound 4).
d) 3-(2-Methoxy-10,11-dihydro-dibenzo(b,f)oxepin-10-yl)-8-methyl-3,8-diazabicyclo(3.2.1)octane (Compound 5).
e) 3-(2-Methylthio-10,11-dihydro-dibenzo[b,f]oxepin-10-yl)-8-methyl-3,8-diazabicyclo(3.2.1)octane (Compound 6)
f) 3-(2-Chloro-10,11-dihydro-dibenzo[b,f]oxepin-10-yl)-8-methyl-3,8-diazabicyclo(3.2.1)octane (Compound 7).
g) 3-(2-Methyl-10,11-dihydro-dibenzo[b,f]oxepin-10-yl)-8-methyl-3,8-diazabicyclo(3.2.1)octane (Compound 8).
h) 3-(2-Chloro-dibenzo[b,f]cycloheptan-10-yl)-8-methyl-3,8-diazabicyclo(3.2.1)octane (Compound 9).
i) 3-(2-Methyl-dibenzo[b,f]cycloheptan-10-yl)-8-methyl-3,8-diazabicyclo(3.2.1)octane (Compound 10).
j) 8-(2-Chloro-10,11-dibydro-dibenzo[b.f]oxepin-10-yl)-3-methyl-3,8-diazabicyclo(3.2.1)octane (Compound 11).
k) 8-(2-Methyl-10,11-dihydro-dibenzo[b,f]oxepin-10-yl)-3-methyl-3,8-diazabicyclo(3.2.1)octane (Compound 12).
l) 3-(2-Methanesulfonyl-dibenzo[b,f]cycloheptan-10-yl)-8-methyl-3,8-diazabicyclo(3.2.1)octane (Compound 13).
m) 3-(2,4-Dichloro-10,11-dihydro-dibenzo[b,f]oxepiun-10-yl)-8-methyl-3,8-diazabicyclo(3.2.1)octane (Compound 14).
n) 3-(2-Chloro-10H-dibenzo[b,f]oxepin-11-one-10-yl)-8-methyl-3,8-30 diazabicyclo(3.2.1)octane (Compound 15).

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A pharmaceutical composition, comprising a compound of the formula:

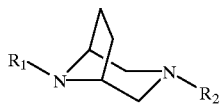

wherein:

R₁ represents hydrogen or straight or branched chain lower alkyl having 1–6 carbon atoms and R₂ represents a group of the formula:

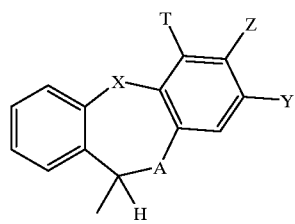

or

R₂ represents hydrogen or straight or branched chain lower alkyl having 1–6 carbon atoms and R₁ represents a group of the formula:

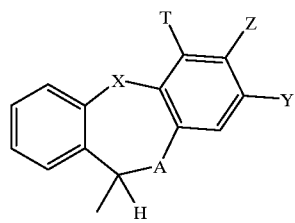

wherein

X is oxygen, methylene, or NH;

Y is halogen, straight or branched chain lower alkyl having 1–6 carbon atoms, lower alkoxy having 1–6 carbon atoms, hydroxy, amino, aminoalkyl where the alkyl is straight or branched chain lower alkyl having 1–6 carbon atoms, $SR_3$, $SOR_3$, or $SO_2R_3$ where $R_3$ is straight or branched chain lower alkyl having 1–6 carbon atoms, or $SO_2NR_4R_5$ where $R_4$ and $R_5$ are the same or different and represent hydrogen or straight or branched chain lower alkyl having 1–6 carbon atoms;

Z is hydrogen, amino or $NHR_6$ where $R_6$ is lower alkyl having 1–6 carbon atoms;

T is hydrogen, halogen, hydroxy, or lower alkoxy having 1–6 carbon atoms; and

A is methylene, carbonyl or CHOH together—with at least one pharmaceutically acceptable carrier.

2. A method for treatment of schizophrenia, depression, Parkinsonism, or the extrapyramidal side effects associated with the use of conventional neuroleptic agents, which comprises administering to a patient in need of such treatment a compound of the formula:

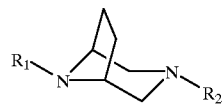

wherein:

R¹ represents hydrogen or straight or branched chain lower alkyl having 1–6 carbon atoms and $R_2$ represents a group of the formula:

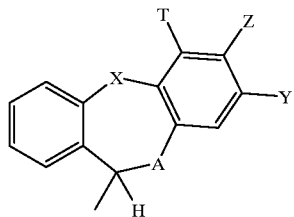

or

R₂ represents hydrogen or straight or branched chain lower alkyl having 1–6 carbon atoms and $R_1$ represents a group of the formula:

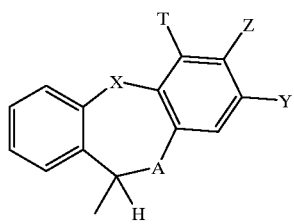

wherein

X is oxygen, methylene, or NH;

Y is halogen, straight or branched chain lower alkyl having 1–6 carbon atoms, lower alkoxy having 1–6 carbon atoms, hydroxy, amino, aminoalkyl where the alkyl is straight or branched chain lower alkyl having 1–6 carbon atoms, $SR_3$, $SOR_3$, or $SO_2R_3$ where $R_3$ is straight or branched chain lower alkyl having 1–6 carbon atoms, or $SO_2NR_4R_5$ where $R_4$ and $R_5$ are the same or different and represent hydrogen or straight or branched chain lower alkyl having 1–6 carbon atoms;

Z is hydrogen, amino or $NHR_6$ where $R_6$ is lower alkyl having 1–6 carbon atoms;

T is hydrogen, halogen, hydroxy, or lower alkoxy having 1–6 carbon atoms; and

A is methylene, carbonyl or CHOH; to a patient in need thereof.

3. A method according to claim 2, where the disorder is schizophrenia or depression.

4. A method according to claim 2, where the disorder is extrapyramidal side effects associated with neuroleptic agents.

5. A method according to claim 2, where the disorder is Parkinsonism.

* * * * *